(12) United States Patent
Reece

(10) Patent No.: US 9,837,679 B2
(45) Date of Patent: Dec. 5, 2017

(54) METAL COMPLEXES OF SUBSTITUTED CATECHOLATES AND REDOX FLOW BATTERIES CONTAINING THE SAME

(71) Applicant: LOCKHEED MARTIN ADVANCED ENERGY STORAGE, LLC, Bethesda, MD (US)

(72) Inventor: Steven Y. Reece, Cambridge, MA (US)

(73) Assignee: Lockheed Martin Advanced Energy Storage, LLC, Bethesda, MD (US)

( * ) Notice: Subject to any disclaimer, the term of this patent is extended or adjusted under 35 U.S.C. 154(b) by 0 days.

(21) Appl. No.: 14/952,899

(22) Filed: Nov. 25, 2015

(65) Prior Publication Data

US 2016/0149251 A1 May 26, 2016

Related U.S. Application Data

(60) Provisional application No. 62/084,638, filed on Nov. 26, 2014.

(51) Int. Cl.
*H01M 8/18* (2006.01)
*C07F 7/28* (2006.01)

(52) U.S. Cl.
CPC ........... *H01M 8/188* (2013.01); *C07F 7/28* (2013.01); *H01M 2300/0002* (2013.01); *Y02E 60/528* (2013.01)

(58) Field of Classification Search
CPC ............ C07F 7/28; H01M 8/20; H01M 8/188
See application file for complete search history.

(56) References Cited

U.S. PATENT DOCUMENTS

| | | | |
|---|---|---|---|
| 1,279,295 A | 9/1918 | Downs | |
| 2,353,782 A | 7/1944 | Neumark | |
| 2,415,792 A | 2/1947 | Gravell | |
| 3,294,588 A | 12/1966 | Morton | |
| 3,425,796 A | 2/1969 | Bauer | |
| 3,428,654 A | 2/1969 | Rubinfeld | |
| 3,573,984 A | 4/1971 | Shah | |
| 3,707,449 A | 12/1972 | Reinhardt et al. | |
| 3,772,379 A | 11/1973 | Woodgate | |
| 3,876,435 A | 4/1975 | Dollman | |
| 3,916,004 A * | 10/1975 | Okada | A61K 31/198 556/116 |
| 3,919,000 A | 11/1975 | Yarrington | |
| 3,920,756 A | 11/1975 | Tahara et al. | |
| 3,929,506 A | 12/1975 | Leddy et al. | |
| 3,985,517 A | 10/1976 | Johnson | |
| 3,985,585 A | 10/1976 | Tuttle et al. | |
| 4,046,861 A | 9/1977 | Reinhardt et al. | |
| 4,064,324 A | 12/1977 | Eustace | |
| 4,069,371 A | 1/1978 | Zito | |
| 4,126,529 A | 11/1978 | DeBerry | |
| 4,180,623 A | 12/1979 | Adams | |
| 4,202,799 A | 5/1980 | Yoshimura et al. | |
| 4,233,144 A | 11/1980 | Pace et al. | |
| 4,362,791 A | 12/1982 | Kaneko et al. | |
| 4,378,995 A | 4/1983 | Gratzfeld et al. | |
| 4,410,606 A | 10/1983 | Loutfy et al. | |
| 4,436,711 A | 3/1984 | Olson | |
| 4,436,712 A | 3/1984 | Olson | |
| 4,436,713 A | 3/1984 | Olson | |
| 4,436,714 A | 3/1984 | Olson | |
| 4,443,423 A | 4/1984 | Olson | |
| 4,443,424 A | 4/1984 | Olson | |
| 4,468,441 A | 8/1984 | D'Agostino et al. | |
| 4,485,154 A | 11/1984 | Remick et al. | |
| 4,520,083 A | 5/1985 | Prater et al. | |
| 4,563,403 A | 1/1986 | Julian | |
| 4,592,973 A | 6/1986 | Pemsler et al. | |

(Continued)

FOREIGN PATENT DOCUMENTS

| CN | 1284208 A | 2/2001 |
|---|---|---|
| CN | 101877412 A | 11/2010 |

(Continued)

OTHER PUBLICATIONS

Xu, Z.—Mechanics of metal-catecholate complexes: The roles of coordination state and metal types, Scientific Reports, 3:2914, pp. 1-7, published on Oct. 10, 2013.*

Santhee Devi, K.V.; Rama Raju B.; Nageswara Rao, G.—ph-metric Investigation on Mixed-Ligand Complexes of Ca(II), Mg(II) and Zn(II) with L-Dopa and 1,10-Phenantroline in Propylene glycol-Water Mixtures, RRJC, vol. 1, issue 1, Oct.-Dec. 2012.*

Sheik Mansoor, S.-Mixed Metal Complexes of Copper (II), Nickel (II) and Zinc(II) Involving Dopa and Dopamine, International Journal of ChemTech Research, vol. 2, No. 1, pp. 640-645, Jan.-Mar. 2010.*

(Continued)

*Primary Examiner* — Anca Eoff
(74) *Attorney, Agent, or Firm* — McDermott Will & Emery LLP

(57) ABSTRACT

Active materials for flow batteries can include various coordination compounds formed from transition metals. Some compositions containing coordination compounds can include a substituted catecholate ligand having a structure of

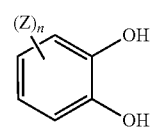

in a neutral form or a salt form, in which Z is a heteroatom functional group bound to the substituted catecholate ligand at an open aromatic ring position and n is an integer ranging between 1 and 4. When more than one Z is present, each Z can be the same or different. Electrolyte solutions can include such coordination compounds, and such electrolyte solutions can be incorporated within a flow battery.

15 Claims, 1 Drawing Sheet

(56) References Cited

U.S. PATENT DOCUMENTS

| | | | |
|---|---|---|---|
| 4,617,244 A | 10/1986 | Greene | |
| 4,680,308 A | 7/1987 | Schwartz et al. | |
| 4,818,646 A | 4/1989 | Takakubo et al. | |
| 4,880,758 A | 11/1989 | Heistand, II et al. | |
| 4,952,289 A | 8/1990 | Ciccone et al. | |
| 4,959,135 A | 9/1990 | Zenner et al. | |
| 4,973,720 A | 11/1990 | Saito et al. | |
| 5,084,533 A | 1/1992 | Shah et al. | |
| 5,122,461 A | 6/1992 | Hsiung et al. | |
| 5,264,097 A | 11/1993 | Vaughan | |
| 5,302,481 A | 4/1994 | Ong | |
| 5,318,865 A | 6/1994 | Kaneko et al. | |
| 5,433,934 A | 7/1995 | Chang et al. | |
| 5,472,807 A | 12/1995 | Licht et al. | |
| 5,643,670 A | 7/1997 | Chung | |
| 5,679,239 A | 10/1997 | Blum et al. | |
| 5,759,711 A | 6/1998 | Miyabayashi et al. | |
| 5,785,841 A | 7/1998 | Tseng | |
| 5,876,581 A | 3/1999 | Itaya et al. | |
| 5,910,366 A | 6/1999 | Chowdhury et al. | |
| 6,001,326 A | 12/1999 | Kim et al. | |
| 6,030,517 A | 2/2000 | Lincot et al. | |
| 6,054,230 A | 4/2000 | Kato | |
| 6,461,772 B1 | 10/2002 | Miyake et al. | |
| 6,475,661 B1 | 11/2002 | Pellegri et al. | |
| 6,485,868 B1 | 11/2002 | Tsujioka et al. | |
| 6,555,989 B1 | 4/2003 | Pearson | |
| 6,585,951 B1 | 7/2003 | Hong et al. | |
| 6,624,328 B1 | 9/2003 | Guerra | |
| 7,046,418 B2 | 5/2006 | Lin et al. | |
| 7,193,764 B2 | 3/2007 | Lin et al. | |
| 7,223,833 B1 | 5/2007 | Nielsen et al. | |
| 7,252,905 B2 | 8/2007 | Clarke et al. | |
| 7,265,162 B2 | 9/2007 | Yandrasits et al. | |
| 7,348,088 B2 | 3/2008 | Hamrock et al. | |
| 7,463,917 B2 | 12/2008 | Martinez | |
| 7,508,568 B2 | 3/2009 | Lin et al. | |
| 7,550,231 B2 | 6/2009 | Stauffer | |
| 7,557,164 B2 | 7/2009 | Felix et al. | |
| 7,625,663 B2 | 12/2009 | Clarke et al. | |
| 7,645,540 B2 | 1/2010 | Boone et al. | |
| 7,678,728 B2 | 3/2010 | Olson et al. | |
| 7,745,056 B2 | 6/2010 | Lee et al. | |
| 7,767,777 B2 | 8/2010 | Buesing et al. | |
| 7,927,731 B2 | 4/2011 | Sahu | |
| 7,931,981 B2 | 4/2011 | Boone et al. | |
| 7,935,366 B2 | 5/2011 | Pahuja et al. | |
| 7,998,335 B2 | 8/2011 | Feeney et al. | |
| 8,129,554 B2 | 3/2012 | Schwaiger | |
| 8,187,441 B2 | 5/2012 | Evans et al. | |
| 8,445,118 B2 | 5/2013 | Cordonier et al. | |
| 8,492,581 B2 | 7/2013 | Frost | |
| 8,691,413 B2 | 4/2014 | Esswein et al. | |
| 8,753,761 B2 | 6/2014 | Esswein et al. | |
| 9,300,000 B2 | 3/2016 | Jansen et al. | |
| 9,382,274 B2 | 7/2016 | Esswein et al. | |
| 9,409,842 B1 | 8/2016 | Fu et al. | |
| 2002/0177042 A1 | 11/2002 | Amendola | |
| 2003/0068561 A1 | 4/2003 | Okahara et al. | |
| 2003/0143456 A1 | 7/2003 | Kazacos et al. | |
| 2003/0228394 A1 | 12/2003 | Abdel-Monem et al. | |
| 2004/0096746 A1 | 5/2004 | Wietelmann et al. | |
| 2005/0098437 A1 | 5/2005 | Shiepe | |
| 2005/0244707 A1 | 11/2005 | Skyllas-Kazacos et al. | |
| 2006/0047094 A1 | 3/2006 | Cherkasov et al. | |
| 2007/0275291 A1 | 11/2007 | Gu et al. | |
| 2008/0274385 A1 | 11/2008 | Creeth | |
| 2008/0292964 A1 | 11/2008 | Kazacos et al. | |
| 2009/0110998 A1 | 4/2009 | Miyachi et al. | |
| 2009/0130525 A1 | 5/2009 | Miyachi et al. | |
| 2009/0208807 A1 | 8/2009 | Miyachi et al. | |
| 2009/0308752 A1 | 12/2009 | Evans et al. | |
| 2010/0003586 A1 | 1/2010 | Sahu | |
| 2010/0059388 A1 | 3/2010 | Clarke et al. | |
| 2010/0086823 A1 | 4/2010 | Koshino et al. | |
| 2010/0086983 A1* | 4/2010 | Gellett | B01D 53/1475 435/168 |
| 2010/0239946 A1 | 9/2010 | Miyachi et al. | |
| 2011/0014532 A1 | 1/2011 | Knuckey et al. | |
| 2011/0136016 A1 | 6/2011 | Huang et al. | |
| 2011/0189549 A1 | 8/2011 | Sun et al. | |
| 2011/0195283 A1 | 8/2011 | Sun et al. | |
| 2011/0200890 A1 | 8/2011 | Kocherginsky | |
| 2011/0223450 A1 | 9/2011 | Horne et al. | |
| 2011/0244277 A1 | 10/2011 | Gordon, II et al. | |
| 2011/0244367 A1 | 10/2011 | Watahiki et al. | |
| 2012/0052347 A1 | 3/2012 | Wilson et al. | |
| 2012/0077095 A1 | 3/2012 | Roumi et al. | |
| 2012/0107661 A1 | 5/2012 | Lee et al. | |
| 2012/0135278 A1 | 5/2012 | Yoshie et al. | |
| 2012/0171541 A1 | 7/2012 | Park et al. | |
| 2012/0183868 A1 | 7/2012 | Toussaint et al. | |
| 2012/0196188 A1 | 8/2012 | Zhang et al. | |
| 2012/0202099 A1 | 8/2012 | Perry et al. | |
| 2012/0208061 A1 | 8/2012 | Sahu et al. | |
| 2012/0244406 A1 | 9/2012 | Xia et al. | |
| 2012/0263990 A1 | 10/2012 | Kim | |
| 2013/0004819 A1 | 1/2013 | Mun et al. | |
| 2013/0157087 A1 | 6/2013 | Pandy et al. | |
| 2013/0252062 A1 | 9/2013 | Wilkins et al. | |
| 2013/0252137 A1 | 9/2013 | Zhang et al. | |
| 2014/0028260 A1 | 1/2014 | Goeltz et al. | |
| 2014/0028261 A1 | 1/2014 | Esswein et al. | |
| 2014/0030572 A1 | 1/2014 | Esswein et al. | |
| 2014/0030573 A1 | 1/2014 | Esswein et al. | |
| 2014/0030631 A1 | 1/2014 | Esswein et al. | |
| 2014/0051003 A1 | 2/2014 | Esswein et al. | |
| 2014/0080035 A1 | 3/2014 | Esswein et al. | |
| 2014/0138576 A1 | 5/2014 | Esswein et al. | |
| 2014/0178735 A1 | 6/2014 | Wang et al. | |
| 2014/0193687 A1 | 7/2014 | Park et al. | |
| 2014/0239906 A1 | 8/2014 | Anderson et al. | |
| 2014/0274936 A1* | 9/2014 | Piccariello | A61K 31/165 514/43 |
| 2014/0349177 A1* | 11/2014 | Chung | H01M 10/0568 429/200 |
| 2014/0377666 A1 | 12/2014 | Kodama et al. | |
| 2015/0236543 A1 | 8/2015 | Brushett et al. | |
| 2015/0372333 A1 | 12/2015 | Odom et al. | |
| 2016/0066578 A1* | 3/2016 | Ala'Aldeen | A61Q 11/00 424/404 |
| 2016/0208165 A1* | 7/2016 | Li | C23F 11/10 |
| 2016/0264603 A1 | 9/2016 | Esswein et al. | |
| 2016/0268623 A1 | 9/2016 | Esswein et al. | |
| 2016/0272659 A1 | 9/2016 | King et al. | |
| 2016/0276693 A1 | 9/2016 | Goeltz et al. | |
| 2016/0276694 A1 | 9/2016 | Goeltz et al. | |
| 2016/0276695 A1 | 9/2016 | Esswein et al. | |
| 2017/0253620 A1 | 9/2017 | Humbarger et al. | |
| 2017/0256811 A1 | 9/2017 | Humbarger et al. | |
| 2017/0271704 A1 | 9/2017 | Morris-Cohen | |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-97/17354 A1 | 5/1997 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |

(56) References Cited

FOREIGN PATENT DOCUMENTS

| WO | WO-2013/006427 A1 | 1/2013 |
|---|---|---|
| WO | WO-2013/048603 A1 | 4/2013 |
| WO | WO-2015/069439 A1 | 5/2015 |

OTHER PUBLICATIONS

Abdulghani, A.J., Noori Khaleel, A.M.—Preparation and Characterization of Di-, Tri-, and Tetranuclear Schiff Base Complexes Derived from Diamines and 3,4-Dihydroxybenzaldehyde, Hindawi Publishing Corporation, Bioinorganic Chemistry and Applications, vol. 2013, pp. 1-14, 2013.*
Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
Bosch et al., "Novel Catalysis of Hydroquinone Autoxidation with Nitrogen Oxides," J. Org. Chem., 1994, pp. 2529-2536, 59.
Lang et al., "Studies on the Biosynthesis of Bovilactone-4,4 and Related Fungal Meroterpenoids," Eur. J. Org. Chem., 2008, pp. 3544-3551.
Lang et al., "Studies on the Structure and Biosynthesis of Tridentoquinone and Related Meroterpenoids from the Mushroom *Suillus tridentinus* (Boletales)," Eur. J. Org. Chem., 2008, pp. 816-825.
Mcomie et al. "The Thiele-Winter Acetoxylation of Quinones," Organic Reactions, 1972, pp. 199-277, 19, John Wiley and Sons, Inc., New York.
Spyroudis, "Hydroxyquinones: Synthesis and Reactivity," Molecules, 2000, pp. 1291-1330, 5.
W. Maison, et al., "Effect of Calcination Temperature on Phase Transformation and Particle size of Barium Titanate Fine Powders Synthesized by the Catecholate Process," ScienceAsia, 2001, pp. 239-243, 27.
Borgias, "Synthetic, structural, and physical studies of titanium complexes of catechol and 3,5-di-tert-butylcatechol," Inorg. Chem., Apr. 1984, 23(8), 1009-1016.
Brezina, "Study of the reduction of oxygen on a carbon paste electrode in an alkaline medium," Coll. Czech. Chem. Commun., 1973, 38(10), 3024-3031.
Caulton, "Systematics and Future Projections Concerning Redox-Noninnocent Amide/Imine Ligands," Eur. J. Inorg. Chem., Jan. 2012, 2012(3), 435-443.
Cerofontain et al. "Sulfonation and sulfation on reaction of 1,2-dihydroxybenzene and its methyl ethers in concentrated aqueous sulfuric acid," Recl Trav Chim Pays-Bas, 1988, pp. 325-330, vol. 107.
Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.
Cohen, "The Association of Ferrocyanide Ions With Various Cations," J. Phys. Chem., Aug. 1957, 61(8), 1096-1100.
Davies, "Electroceramics from Source Materials via Molecular Intermediates: PbTiO3 from TiO2 via [Ti(catecholate)3]2-," J. Am. Ceram. Soc., Aug. 1990, 73(8), 2570-2572.
Dehaen et al, "A Self-Assembled Complex with a Titanium (IV) Catecholate Core as a Potential Bimodal Contrast Agent," Chem Eur J, 2012, pp. 293-302, vol. 18.
Fryda, "Wastewater Treatment With Diamond Electrodes," Diamond Materials, Electrochemical Society Proceedings, 2000, 99(32), 473-483.
Gail, "Cyano Compounds, Inorganic" in Ullmann's Encyclopedia of Industrial Chemistry, 2012, 10, 674-710.
Hollandsworth, "Zinc/Ferrocyanide Battery Development Phase IV" Lockheed Missiles and Space Company, Inc., Contractor report, Sandia Contract DE-AC04-76DP00789, May 1985, 278 pages.
Kim, "Novel catalytic effects of Mn3O4 for all vanadium redox flow batteries," Chem. Commun., Apr. 2012, 48(44), 5455-5457.
Kulesza, "Electrochemical preparation and characterization of hybrid films composed of Prussian blue type metal hexacyanoferrate and conducting polymer," Electrochimica Acta, Aug. 2001, 46(26-27), 4065-4073.
Leung, "Development of a Zinc-Cerium Redox Flow Battery", 2011, 352 pages.
Leung, "An undivided zinc-cerium redox flow battery operating at room temperature (295 K)," Electrochemistry Communications, 2011, vol. 13, pp. 770-773.
Leung, "Ce(III)/Ce(IV) in methanesulfonic acid as the positive half cell of a redox flow battery," Electrochimica Acta, 2011, vol. 56, pp. 2145-2153.
Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.
Leung, "Characterization of a zinc-cerium flow battery," Journal of Power Sources, 2011, vol. 195, pp. 5174-5185.
Modiba, "Electrochemical impedance spectroscopy study of Ce(IV) with aminopolycarboxylate ligands for redox flow batteries applications," Journal of Power Sources, May 2012, vol. 205, 1-9.
Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Nguyen, "Flow Batteries," The Electrochemical Society Interface, Fall 2010, 19(3), 54-56.
Pharr, "Infrared Spectroelectrochemical Analysis of Adsorbed *Hexacyanoferrate* Species Formed during Potential Cycling in the Ferrocyanide/Ferricyanide Redox Couple," Anal. Chem., Nov. 1997, 69(22), 4673-4679.
Raymond, "Coordination isomers of biological iron transport compounds. VI. Models of the enterobactin coordination site. A crystal field effect in the structure of potassium tris( catecholato)chromate( III) and -ferrate( III) sesq u ihyd rates, K3[M( 02C6H4 )3]. 1 . 5H2O, M=chromium, iron," J. Am Chem. Soc., Mar. 1976, 98(7), 1767-1774.
Saito et al. "DPPH radical-scavenging reaction of protocatechuic acid: differnce in reactivity between acids and their esters," Helv Chim Acta, 2006, pp. 1395-1407, vol. 89.
Sever et al, "Visible absorption spectra of metal-catecholate and metal-tironate complexes," Dalton Trans., pp. 1061-1072, 2004.
Sigma-Aldrich Tris(hydroxymethyl)aminomethane, 2015.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4.
Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of The Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, The David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.
Wang, "Determination of iron, titanium, osmium, and aluminum with tiron by reversephase high PERFORMANCE liquid chromatography/electrochemistry," Microchem. J., Jun. 1991, 43(3), 191-197.
Weber, "Redox flow batteries: a review," Journal of Applied Electrochemistry, Oct. 2011, 41(10), 1137-1164.

(56) References Cited

OTHER PUBLICATIONS

Murakami et al., "The Chelating Behavior of Catechol-4-sulfonate with Iron(III) Ion," Bulletin of the Chemical Society of Japan, 1963, pp. 1408-1411; vol. 36.

Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.

Soloveichik, "Flow Batteries: Current Status and Trends," 2015, Chem. Rev., 115 (20), pp. 11533-11558.

Davies, "Electroceramics from Source Materials via Molecular Intermediates: $BaTiO_3$ from $TiO_2$ via $[Ti(catecholate)_3]^{2-}$," May 1990, J. Am. Ceram. Soc., Aug. 1990, 73(5), 1429-30.

Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.

Vliet et al., "Hydroxyhydroquinone Triacetate," Organic Synthesys, 1941, Coll vol. 1, p. 317 (1941), vol. 4, p. 35 (1925) 3 pages.

International Search Report and Written Opinion dated Jan. 19, 2017 from International Application No. PCT/US16/58433.

International Search Report and Written Opinion dated Feb. 17, 2017 from International Application No. PCT/US16/65159.

IUPAC Compendium of Chemical Terminology, "coordinatively unsaturated complex," 1997, http://old.iupac.org/goldbook/C01334.pdf.

International Search Report and Written Opinion from PCT/US17/14764, dated Apr. 20, 2017.

International Search Report and Written Opinion from PCT/US16/69190, dated May 3, 2017.

International Search Report and Written Opinion from PCT/US2017/022203, dated Jun. 6, 2017.

Ahluwalia et al., Intermediates for Organic Synthesis, Chapter 1, Phenols, Sections 1.21 and 1.23, (2003), I.K. International Pvt. Ltd.

Wang et al., "Issues in Freeze Drying of Aqueous Solutions," Chinese Journal of Chemical Engineering, 2012, 20(3), pp. 551-559.

\* cited by examiner

METAL COMPLEXES OF SUBSTITUTED CATECHOLATES AND REDOX FLOW BATTERIES CONTAINING THE SAME

CROSS-REFERENCE TO RELATED APPLICATIONS

The present application claims the benefit of priority under 35 U.S.C. §119 from U.S. Provisional Patent Application 62/084,638, filed on Nov. 26, 2014 and incorporated herein by reference in its entirety.

STATEMENT REGARDING FEDERALLY SPONSORED RESEARCH OR DEVELOPMENT

Not applicable.

FIELD

The present disclosure generally relates to energy storage and, more specifically, to flow batteries and flow battery systems containing coordination compounds.

BACKGROUND

Electrochemical energy storage systems, such as batteries, supercapacitors and the like, have been widely implemented for large-scale energy storage applications. Various battery designs, including flow batteries, have been adopted for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell. The battery is charged or discharged through electrochemical reactions of the active materials that occur inside the cell. Existing flow batteries have suffered from their reliance on battery chemistries and cell designs that result in high cell resistance and/or active materials that cross over the membrane and mix with the opposing electrolyte solution. This phenomenon results in diminished energy storage performance (e.g., round trip energy efficiency) and poor cycle life, among other factors. Despite significant development efforts, no commercially viable flow battery technologies have yet achieved this desirable combination of properties.

In view of the foregoing, improved active materials and electrolyte solutions for electrochemical energy storage would be highly desirable. The present disclosure satisfies the foregoing needs and provides related advantages as well.

SUMMARY

In some embodiments, the present disclosure provides compositions containing a coordination compound having a substituted catecholate ligand. The substituted catecholate ligand has a structure of

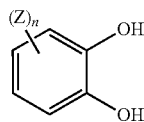

in a neutral form or a salt form. Z is a heteroatom functional group selected from the group consisting of $A^1R^{41}$, $A^2R^{42}$, $A^3R^{43}$, and CHO. Variable n is an integer ranging between 1 and 4, such that one or more Z are bound to the substituted catecholate ligand at an open aromatic ring position. Each Z is the same or different when more than one Z is present. $A^1$ is $-(CH_2)_a-$ or $-(CHOR)(CH_2)_a-$, $R^{41}$ is $-OR^1$ or $-(OCH_2CH_2O)_bR^1$, a is an integer ranging between 0 and about 6, with the proviso that $R^1$ is not H when a is 0 and $R^{41}$ is $-OR^1$, and b is an integer ranging between 1 and about 10. $A^2$ is $-(CH_2)_c-$ or $-CH(OR^2)(CH_2)_d-R^{42}$ is $-NR^3R^4$, a carbon-linked amino acid, or $-C(=O)XR^5$, X is $-O-$ or $-NR^6-$, c is an integer ranging between 0 and about 6, and d is an integer ranging between 0 and about 4. $A^3$ is $-O-$ or $-NR^2-$, $R^{43}$ is $-(CHR^7)_eOR^1$, $-(CHR^7)_e NR^3R^4$, $-(CHR^7)_eC(=O)XR^5$, or $-C(=O)(CHR^7)_fR^8$, e is an integer ranging between 1 and about 6, with the proviso that e is not 1 when $A^3$ is $-O-$, and f is an integer ranging between 0 and about 6. R is H, $C_1$-$C_6$ alkyl, heteroatom-substituted $C_1$-$C_6$ alkyl, or $C_1$-$C_6$ carboxyalkyl. $R^1$ is H, methyl, ethyl, a $C_2$-$C_6$ polyol bound through an ether linkage or an ester linkage, or $C_1$-$C_6$ carboxyalkyl. $R^2$, $R^3$, $R^4$ and $R^6$ are independently selected from the group consisting of H, $C_1$-$C_6$ alkyl, or heteroatom-substituted $C_1$-$C_6$ alkyl. $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or $-(CH_2CH_2O)_bR^1$. $R^7$ is H or OH. $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or $-(OCH_2CH_2O)_bR^1$.

In other various embodiments, the present disclosure provides electrolyte solutions containing a composition having a coordination compound with a substituted catecholate ligand. The substituted catecholate ligand has a structure as defined above.

In still other various embodiments, the present disclosure provides flow batteries incorporating an electrolyte solution containing a composition having a coordination compound with a substituted catecholate ligand. The substituted catecholate ligand has a structure as defined above.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
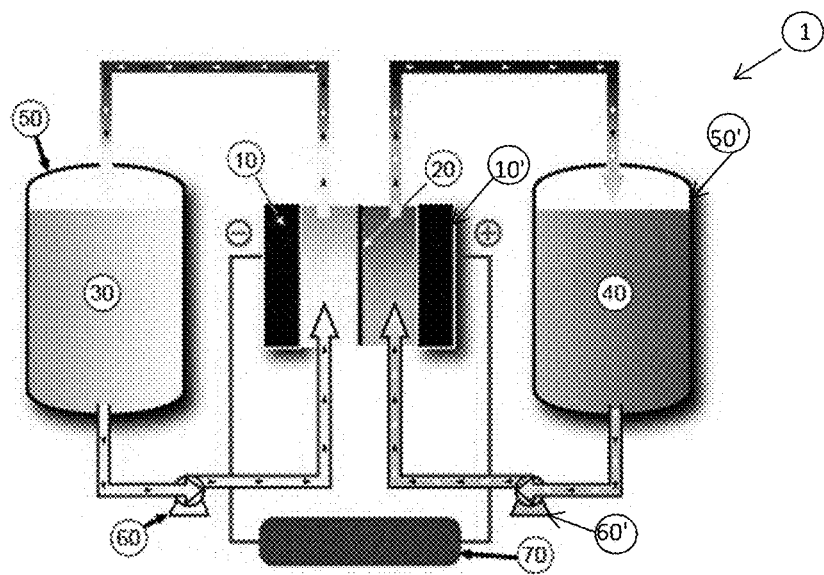
FIG. 1 depicts a schematic of an illustrative flow battery.

The present disclosure is directed, in part, to compositions containing a coordination compound having a substituted catecholate ligand. The present disclosure is also directed, in part, to electrolyte solutions containing a coordination compound having a substituted catecholate ligand. The present disclosure is also directed, in part, to flow batteries containing an electrolyte solution containing a coordination compound having a substituted catecholate ligand.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure describes an electrochemical cell, flow battery, or other energy storage system, it is appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may a representative technique of the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that are operable with high efficiency on a large scale can be highly desirable. Electrochemical energy storage systems, particularly flow batteries, have generated significant interest in this regard, but there remains considerable room for improvement in their operating characteristics. As discussed hereinafter, the active material within the positive and/or negative electrolyte solutions of flow batteries can be modified to provide improved operating characteristics for these electrochemical energy storage systems. Metal-ligand coordination compounds can be particularly beneficial in this regard, and various classes of particularly desirable coordination compounds are discussed hereinafter. Exemplary description of illustrative flow batteries, which can incorporate an electrolyte solution containing one or more of the coordination compounds, and their use and operating characteristics are also described hereinbelow.

As used herein, the terms "active material," "electroactive material," "redox-active material" or variants thereof will refer to materials that undergo a change in oxidation state during operation of an electrochemical energy storage system. When used in electrochemical energy storage systems, such materials can present in dissolved form in an aqueous electrolyte, but they can also be used in suspensions or slurries. As used herein, the term "solution" will refer to the condition of being at least partially dissolved. Since the storage capacity (energy density) of an electrochemical energy storage system often depends on the amount of active material that is present, high-solubility electrolyte solutions can be desirable. From an operational standpoint, freely soluble active materials can be highly desirable in a flow battery in order to avoid deposition of circulating particulates.

Due to their variable oxidation states, transition metals can constitute the positive and/or negative active materials in various embodiments of a flow battery. Cycling between the accessible oxidation states can result in the conversion of chemical energy into electrical energy. Lanthanide elements can be used similarly in this regard.

Coordination compounds of a transition metal or a lanthanide metal can be particularly advantageous when employed as the active material within an electrolyte solution of a flow battery. As used herein, the term "coordination compound" will refer to a metal ion that is complexed by one or more ligands, particularly by at least one chelating ligand. As used herein, the term "chelating ligand" will refer to a ligand that binds a metal ion simultaneously at two or more locations. The chemical nature of the ligands can alter the redox potential of the ligated metal ion, thereby allowing some degree of tailoring to be realized in the operating characteristics of a flow battery incorporating an electrolyte solution containing the coordination compounds. Coordination compounds can also have an altered solubility profile compared to non-ligated metal ions. Depending on the pH of an electrolyte solution and the nature of the ligands, the solubility of a coordination compound in the electrolyte solution can be either higher or lower than that of the corresponding non-ligated metal ion.

Catecholate ligands can be particularly desirable entities for forming coordination compounds to be incorporated within the electrolyte solution of a flow battery. However, unsubstituted catecholate ligands are relatively hydrophobic, and coordination compounds formed from unsubstituted catecholate ligands can have relatively low saturation concentrations in aqueous electrolyte solutions. The low saturation concentrations of unsubstituted catecholate complexes can result in flow batteries having low energy densities.

The present inventor identified various substituted catecholates and their coordination compounds that can provide high saturation solubility levels in electrolyte solutions, particularly aqueous electrolyte solutions, for use in a flow battery. As used herein, the term "substituted catecholate" will refer to a catechol compound (e.g., 1,2-dihydroxybenzene) in which at least one aromatic ring position has been substituted with a heteroatom functional group. As used herein, the term "heteroatom functional group" will refer to any grouping of atoms that contains O or N. The heteroatom functional group(s) of the substituted catecholate ligands can improve the solubility of coordination compounds containing the ligands and/or the pH dependence of the solubility relative to coordination compounds containing an unsubstituted catecholate. The term "unsubstituted catecholate" or just "catecholate" will be used herein to refer to a catechol compound in which none of the open aromatic ring positions have been further substituted. Further description of suitable substituted catecholates and their coordination compounds follows hereinbelow.

Accordingly, the substituted catecholates of the present disclosure and their coordination compounds can desirably provide high-concentration electrolyte solutions for use in flow batteries. The high-concentration electrolyte solutions can improve the energy density and other operating characteristics of flow batteries relative to those attainable using non-ligated transition metal ions or coordination compounds containing only unsubstituted catecholate ligands or other low solubility ligands.

Figure 2:
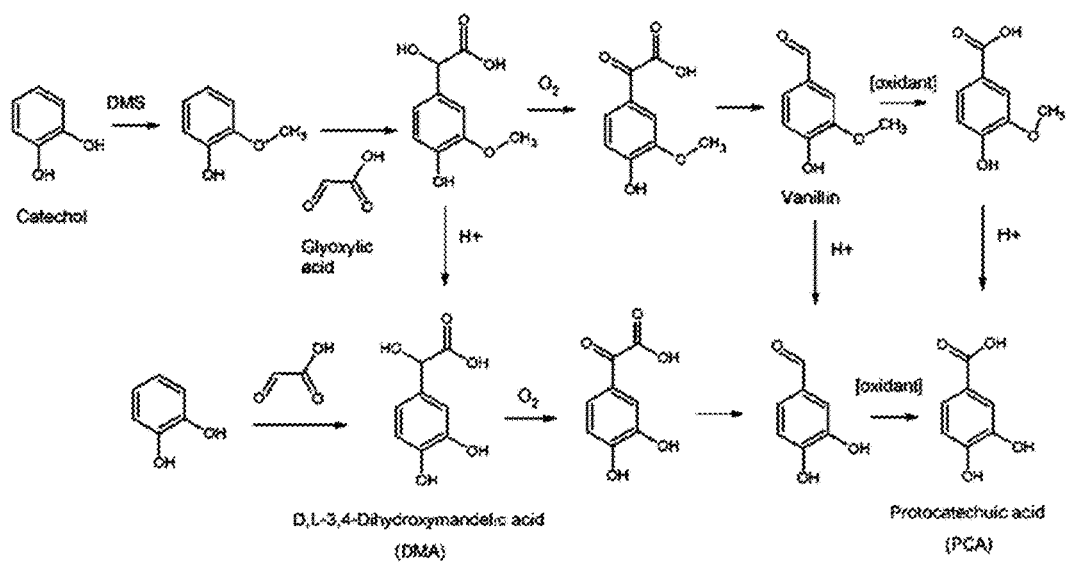
FIG. 2 depicts an illustrative synthetic scheme for preparation of some of the substituted catecholate ligands described herein.

Advantageously, the substituted catecholate ligands of the present disclosure can be produced synthetically by relatively simple series of organic reactions. Illustrative organic reactions that can be used to produce some of the substituted catecholate ligands of the present disclosure are shown in FIG. 2 below. One having ordinary skill in the art can readily determine alternative synthetic pathways, or synthetic pathways for producing any substituted catecholate ligands other than those shown in FIG. 2 below.

Accordingly, compositions containing coordination compounds of substituted catecholate ligands and electrolyte solutions containing such coordination compounds are described herein. Flow batteries incorporating electrolyte solutions containing the substituted catecholate ligands and their coordination compounds are also contemplated in the various embodiments of the present disclosure.

In various embodiments, compositions containing a coordination compound having a substituted catecholate ligand are described herein. The substituted catecholate ligand can have a structure of

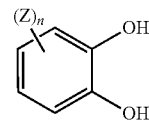

in a neutral form or a salt form. Z is a heteroatom functional group selected from the group consisting of $A^1R^{41}$, $A^2R^{42}$, $A^3R^{43}$, and CHO. Variable n is an integer ranging between 1 and 4, such that one or more Z are bound to the substituted catecholate ligand at an open aromatic ring position. Each Z is the same or different when more than one Z is present. $A^1$ is —$(CH_2)_a$— or —$(CHOR)(CH_2)_a$—, $R^{41}$ is —$OR^1$ or —$(OCH_2CH_2)_bR^1$, a is an integer ranging between 0 and about 6, with the proviso that $R^1$ is not H when a is 0 and $R^{41}$ is —$OR^1$, and b is an integer ranging between 1 and about 10. $A^2$ is —$(CH_2)_c$— or —$CH(OR^2)(CH_2)_d$—$R^{42}$ is —$NR^3R^4$, a carbon-linked amino acid, or —$C(=O)XR^5$, X is —O— or —$NR^6$—, c is an integer ranging between 0 and about 6, and d is an integer ranging between 0 and about 4. $A^3$ is —O— or —$NR^2$—, $R^{43}$ is —$(CHR^7)_eOR^1$, —$(CHR^7)_e$ $NR^3R^4$, —$(CHR^7)_eC(=O)XR^5$, or —$C(=O)$ $(CHR^7)_fR^8$, e is an integer ranging between 1 and about 6, with the proviso that e is not 1 when $A^3$ is —O—, and f is an integer ranging between 0 and about 6. R is H, $C_1$-$C_6$ alkyl, heteroatom-substituted $C_1$-$C_6$ alkyl, or $C_1$-$C_6$ carboxyalkyl. $R^1$ is H, methyl, ethyl, a $C_2$-$C_6$ polyol bound through an ether linkage or an ester linkage, or $C_1$-$C_6$ carboxyalkyl. $R^2$, $R^3$, $R^4$ and $R^6$ are independently selected from the group consisting of H, $C_1$-$C_6$ alkyl, or heteroatom-substituted $C_1$-$C_6$ alkyl. $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or —$(CH_2CH_2O)_bR^1$. $R^7$ is H or OH. $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —$(OCH_2CH_2O)_bR^1$.

With regard to the term "salt form," it is to be understood that this term is directed to any functionalities in Z that may be protonated or deprotonated. Similarly, the term "neutral form" is to be understood in regard to Z being uncharged.

It is to be further understood that the 1,2-dihydroxyl functionalities in the substituted catecholate ligands of the present disclosure are deprotonated when ligated to a metal ion in a coordination compound. Throughout the present disclosure, the protonated "free ligand" form of the substituted catecholate ligands will be shown as a matter of convenience.

The substituted catecholate ligands of the present disclosure can have one, two, three or four Z heteroatom functional groups substituting the open positions of the aromatic ring. When more than one Z is present, each Z heteroatom functional group can be the same or different. In more specific embodiments, the substituted catecholate ligand can have one, two or three Z heteroatom functional groups, such that its structure is among those shown below.

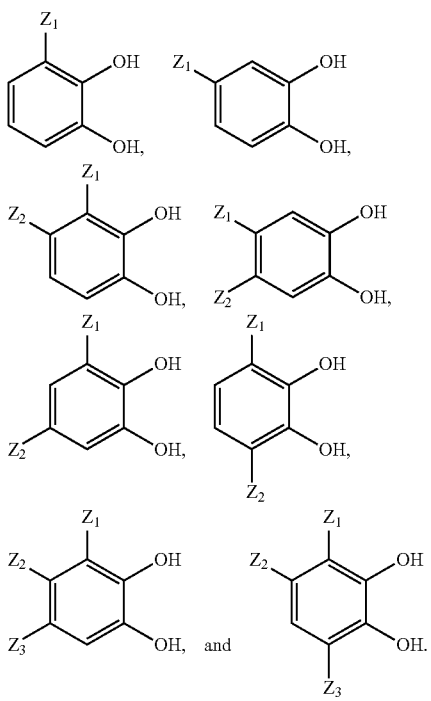

In still more specific embodiments, the substituted catecholate ligand can have one Z functionality, such that its structure is among

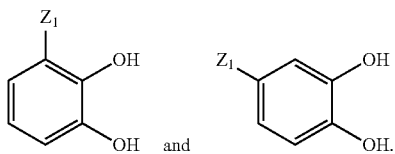

In yet still more specific embodiments, the substituted catecholate ligand can have a formula of

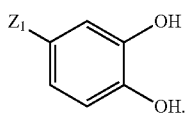

As indicated above, Z can include various heteroatom functional groups that can improve the solubility of the substituted catecholate ligands and their coordination compounds. Illustrative examples of various classes of substituted catecholate ligands incorporating such heteroatom functional groups follows hereinafter.

In some embodiments, Z can be $A^1R^{41}$, wherein $A^1$ is —$(CH_2)_a$— or —$(CHOR)(CH_2)_a$—, $R^{41}$ is —$OR^1$ or —$(OCH_2CH_2O)_bR^1$, a is an integer ranging between 0 and about 6, and b is an integer ranging between 1 and about 10. When $A^1$ is —$(CH_2)_a$— and a is 0, it is to be understood that $R^{41}$ is bound directly to the aromatic ring of the substituted catecholate. Similarly, when $A^1$ is —$(CHOR)(CH_2)_a$— and a is 0, it is to be understood that $R^{41}$ is bound indirectly to the aromatic ring by an intervening —(CHOR) group. In some embodiments of the present disclosure, a can be 0. In other various embodiments of the present disclosure, a can range between 1 and 6, or between 1 and 4, or between 0 and 4, or between 1 and 3.

In the substituted catecholate ligands of the present disclosure, R is H, $C_1$-$C_6$ alkyl, heteroatom-substituted $C_1$-$C_6$ alkyl, or $C_1$-$C_6$ carboxyalkyl, and $R^1$ is H, methyl, ethyl, a $C_3$-$C_6$ alkyl, a heteroatom-substituted $C_3$-$C_6$ alkyl, a $C_2$-$C_6$ polyol bound through an ether linkage or an ester linkage, or $C_1$-$C_6$ carboxyalkyl. That is, at least a portion of $R^{41}$ can be defined by a polyol structure that is bound through an ether linkage or an ester linkage to the remainder of the structure of $R^{41}$, to $A^1$, or to the aromatic ring of the substituted catecholate ligand. Exemplary polyols and their various modes of binding are discussed further below. Illustrative $C_1$-$C_6$ alkyl groups that can be present in any of the various embodiments of the present disclosure can include, for example, methyl, ethyl, propyl, isopropyl, butyl, sec-butyl, tert-butyl, pentyl, isopentyl, neopentyl, 2,2-dimethylbutyl, hexyl, isohexyl, and the like. As used herein, the term "heteroatom-substituted $C_1$-$C_6$ alkyl" will refer to a straight-chain or branched-chain alkyl group that has had one or more of its hydrogen atoms replaced by an oxygen- or nitrogen-containing functional group. "Heteroatom-substituted $C_1$-$C_6$" will also refer to a straight-chain or branched-chain alkyl group that has had one of its backbone carbon atoms and its accompanying hydrogen atoms replaced by an oxygen- or nitrogen-containing functional group.

With regard to $A^1R^{41}$, the following proviso is to be made: $R^1$ is not H when a is 0 and $R^{41}$ is —$OR^1$.

As used herein, the term "polyol" will refer to any compound having two or more alcohol functional groups. Additional heteroatom functionality, such as amines and carboxylic acids, can optionally be present within a polyol. Thus, amino alcohol and hydroxy acid analogues of unmodified glycols and higher polyols are also encompassed by the term "polyol." As used herein, the term "higher polyol" will refer to a polyol having more than two alcohol functional groups. Illustrative polyols that can be present within $R^{41}$ include any $C_2$-$C_6$ polyol, including glycols, higher polyols, and monosaccharides. As with the term "polyol," the term "monosaccharide" is to be understood to also include both the base monosaccharide and the corresponding sugar alcohols, sugar acids, and deoxy sugars of the base monosaccharide, including any open- or closed-chain forms of these materials.

Illustrative polyols that can be present in the various embodiments of the present disclosure include, for example, 1,2-ethanediol (ethylene glycol), 1,2-propanediol (propylene glycol), 1,3-propanediol, 1,2-butanediol, 1,4-butanediol, glycerol, erythritol, threitol, arabitol, xylitol, ribitol, mannitol, sorbitol, galacitol, fucitol, iditol, inositol, glycolaldehyde, glyceraldehyde, 1,3-dihydroxyacetone, erythrose, threose, erythrulose, arabinose, ribose, lyxose, xylose, ribulose, xylulose, allose, altrose, glucose, mannose, gulose, idose, galactose, talose, psicose, fructose, sorbose, tagatose, deoxyribose, rhamnose, fucose, glyceric acid, xylonic acid, gluconic acid, ascorbic acid, glucuronic acid, galacturonic acid, iduronic acid, tartaric acid, galactaric acid, and glucaric acid. Any enantiomeric and/or diastereomeric forms of these compounds are also encompassed within the term "polyol" in the present disclosure, as well as their open- or closed-ring forms, if formed.

More particular embodiments in regard to $A^1R^{41}$ can include, for example, those in which a is 0 or 1, $A^1$ is —$(CH_2)_a$— and $R^{41}$ is —$OR^1$, with the above proviso being made; and a is 0 or 1, $A^1$ is —$(CH_2)_a$— and $R^{41}$ is —$(OCH_2CH_2O)_bR^1$.

In still more particular embodiments in regard to $A^1R^{A1}$, suitable substituted catecholate ligands can include the following:

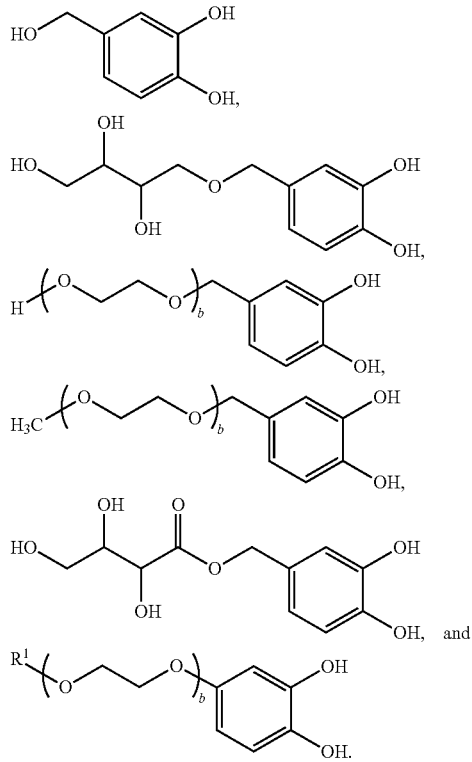

In some embodiments, Z can be $A^2R^{A2}$, wherein $A^2$ is —(CH$_2$)— or —(CH$_2$OR$^2$)(CH$_2$)$_d$—$R^{A2}$ is —NR$^3$R$^4$, a carbon-linked amino acid, or —C(═O)XR$^5$, X is —O— or —NR$^6$—, c is an integer ranging between 0 and about 6, d is an integer ranging between 0 and about 4. $R^2$, $R^3$, $R^4$ and $R^6$ are independently selected from the group consisting of H, C$_1$-C$_6$ alkyl, or heteroatom-substituted C$_1$-C$_6$ alkyl. Likewise, $R^5$ is H, C$_1$-C$_6$ alkyl, heteroatom-substituted C$_1$-C$_6$ alkyl, a C$_2$-C$_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or —(CH$_2$CH$_2$O)$_b$R$^1$, wherein R$^1$ is defined as above. In some embodiments, c can range between 0 and 4, or between 1 and 5, or between 1 and 4, or between 1 and 3. In some embodiments, d can range between 0 and 3, or between 0 and 2, or between 1 and 3.

With regard to carbon-linked amino acids, the amino acids can be carbon-linked by their alpha carbon in various embodiments (i.e., adjacent to the carboxylate and amino functionalities). As used herein, the term "amino acid" will refer to any group of atoms containing at least one amine group and one carboxylic acid group, optionally in protected form. In more specific embodiments, the term "amino acid" will refer to naturally occurring amino acids in their D- or L-forms, including oligomers thereof. Illustrative naturally occurring amino acids that can be present include, for example, arginine, histidine, lysine, aspartic acid, glutamic acid, serine, threonine, asparagine, glutamine, cysteine, glycine, proline, alanine, valine, isolucine, leucine, methionine, phenylalanine, tyrosine, and tryptophan, as well as synthetic derivatives thereof. These amino acids and others can be present in ester-linked or amide-linked forms as discussed further hereinbelow.

More particular embodiments in regard to $A^2R^{A2}$ can include, for example, those in which $A^2$ is —(CH$_2$)$_c$—, c is an integer ranging between 1 and 6, or between 1 and 3, and $R^{A2}$ is —NR$^3$R$^4$ in which R$^3$ and R$^4$ are H or CH$_3$; $A^2$ is —(CH$_2$)$_c$—, c is 0, and $R^{A2}$ is —NR$^3$R$^4$ in which R$^3$ and R$^4$ are H or CH$_3$; $A^2$ is —(CH$_2$)$_c$—, c is 0, and $R^{A2}$ is —C(═O)XR$^5$ in which X is O and R$^5$ is a C$_2$-C$_6$ polyol bound through an ester linkage, a hydroxyacid bound through an ester linkage, a polyglycol acid bound through an ester linkage, an amino alcohol bound through an ester linkage, or an amino acid bound through an ester linkage; $A^2$ is —CH(OR$^2$)(CH$_2$)$_d$—R$^2$ is H, d is an integer ranging between 1 and 4, and $R^{A2}$ is —NR$^3$R$^4$ in which R$^3$ and R$^4$ are H or CH$_3$; and $A^2$ is —CH(OR$^2$)(CH$_2$)$_d$—R$^2$ is H, d is an integer ranging between 1 and 4, and $R^{A2}$ is —C(═O) XR$^5$ in which X is O and R$^5$ is a C$_2$-C$_6$ polyol bound through an ester linkage, a hydroxyacid bound through an ester linkage, a polyglycol acid bound through an ester linkage, an amino alcohol bound through an ester linkage, or an amino acid bound through an ester linkage.

In still more particular embodiments in regard to $A^2R^{A2}$, suitable substituted catecholate ligands can include the following:

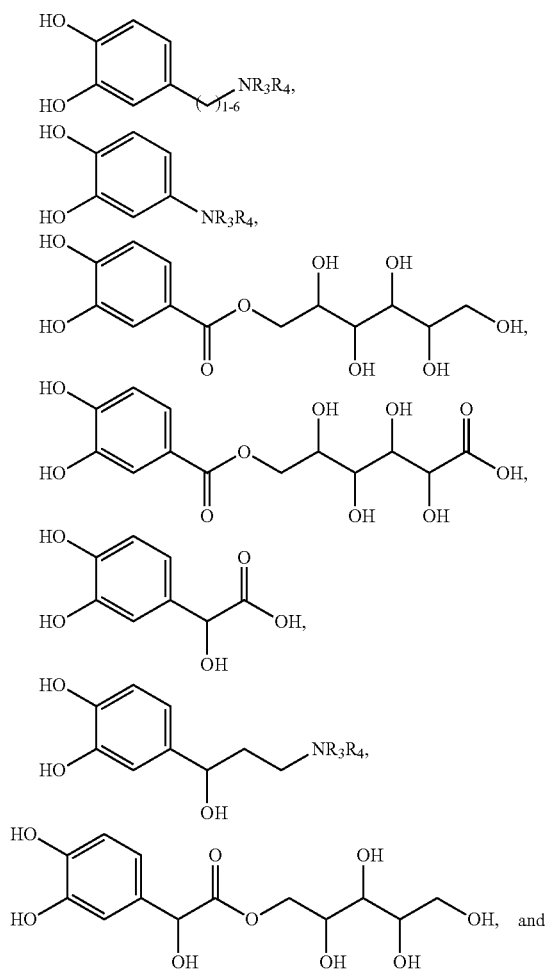

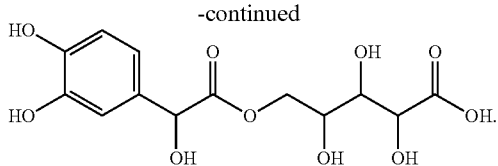

In some embodiments, Z can be $A^3R^{A3}$, wherein $A^3$ is —O— or —NR$^2$—, $R^{A3}$ is —(CHR$^7$)$_e$OR$^1$, —(CHR$^7$)$_e$NR$^3$R$^4$, —(CHR$^7$)$_e$C(=O)XR$^5$, or —(C=O)(CHR$^7$)$_e$R$^8$, e is an integer ranging between 1 and about 6, f is an integer ranging between 0 and about 6, R$^7$ is H or OH, and R$^8$ is h, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —(OCH$_2$CH$_2$O)$_b$R$^1$. In other various embodiments of the present disclosure, e can range between 2 and 6, or between 1 and 4, or between 1 and 3. In other various embodiments of the present disclosure, f can range between 1 and 6, or between 1 and 4, or between 0 and 4, or between 1 and 3.

With regard to $A^3R^{A3}$, the following proviso is to be made: e is not 1 when $A^3$ is —O—.

More particular embodiments in regard to $A^3R^{A3}$ can include, for example, those in which $A^3$ is —O—, $R^{A3}$ is —(CHR$^7$)$_e$OR$^1$, and e is an integer ranging from 2 to 6; $A^3$ is —O—, $R^{A3}$ is —(CHR$^7$)$_e$NR$^3$R$^4$, and e is an integer ranging from 1 to 6; $A^3$ is —O—, $R^{A3}$ is —(CHR$^7$)$_e$C(=O)OR$^5$, and e is an integer ranging from 2 to 6; and $A^3$ is —O—, $R^{A3}$ is —C(=O)(CHR$^7$)$_f$R$^8$, and f is an integer ranging from 0 to 6 or from 1 to 6.

In still more particular embodiments in regard to $A^3R^{A3}$, suitable substituted catecholate ligands can include the following:

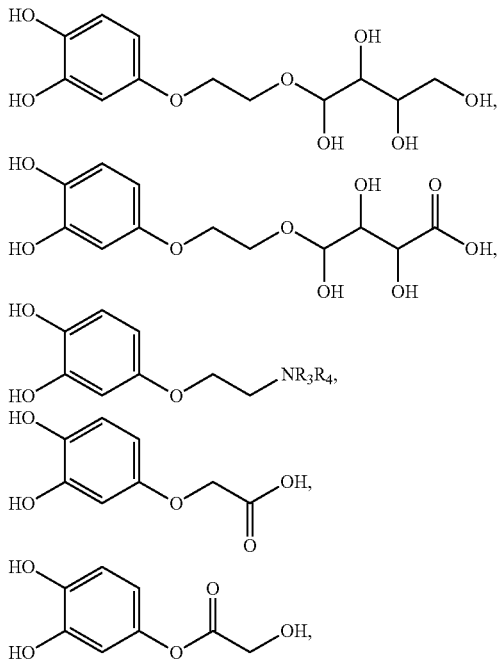

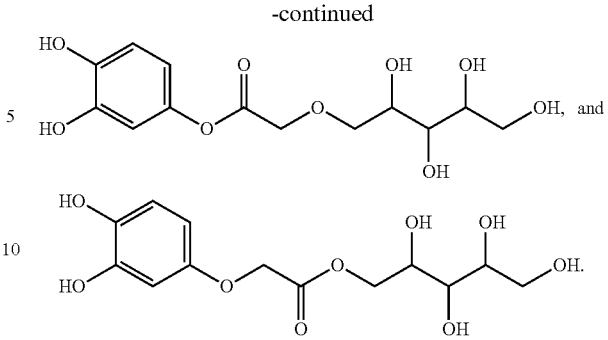

In still other various embodiments of the present disclosure, the substituted catecholate ligand of the present disclosure can have one or more Z that is CHO, as shown in the exemplary structure below.

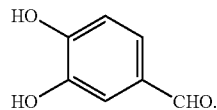

In other more specific embodiments of the present disclosure, the substituted catecholate ligand can have a structure selected from among the following:

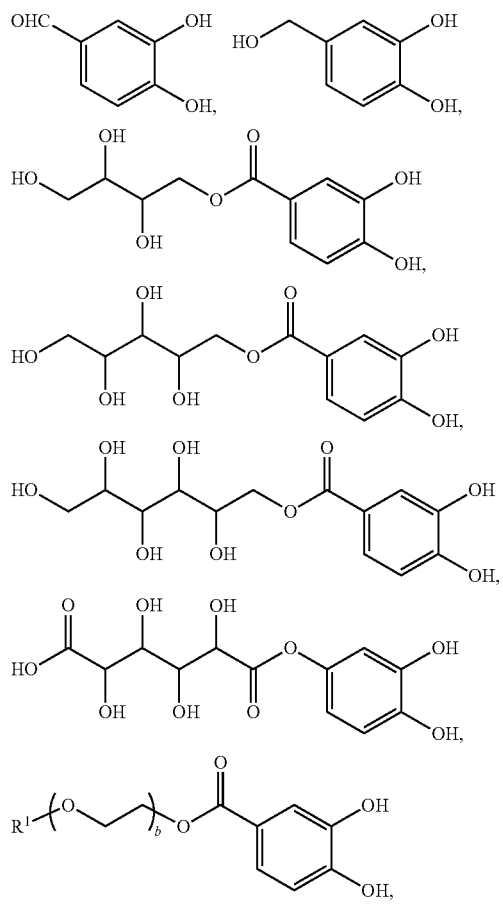

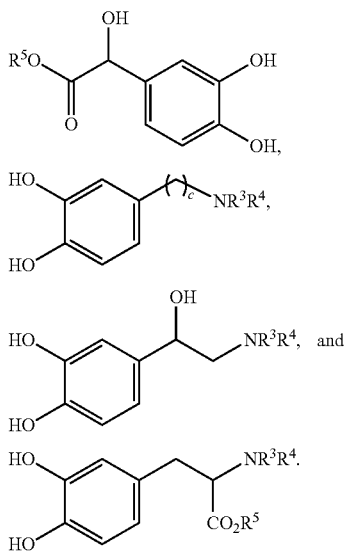

In other more specific embodiments of the present disclosure, the substituted catecholate ligand can have a structure selected from among the following

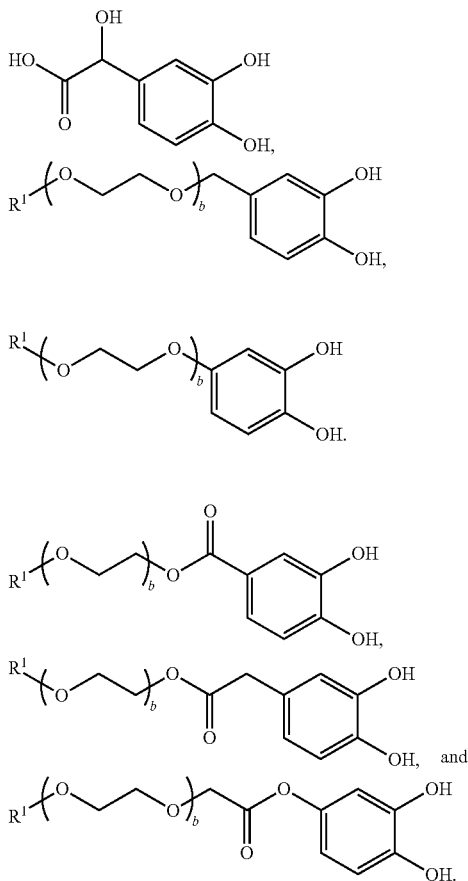

In still other various embodiments of the present disclosure, the substituted catecholate ligand can be 3,4-dihydroxymandelic acid, which has a structure of

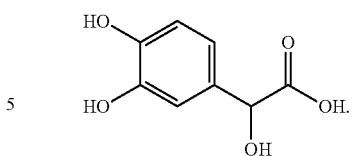

In various embodiments, compositions of the present disclosure can include a coordination compound having at least one substituted catecholate ligand that is selected from among the substituted catecholate ligands defined above. In more specific embodiments, the coordination compound can have a formula of $D_gM(L_1)(L_2)(L_3)$, in which M is a transition metal, D is $NH_4^+$ or tetraalkylammonium ($C_1$-$C_4$ alkyl), $Na^+$, $K^+$ or any combination thereof, g is an integer ranging between 1 and 6, and $L_1$, $L_2$ and $L_3$ are ligands and at least one of $L_1$, $L_2$ and $L_3$ is a substituted catecholate ligand as defined herein.

In some embodiments, at least two of $L_1$, $L_2$ and $L_3$ are substituted catecholate ligands as defined herein. In other various embodiments, each of $L_1$, $L_2$ and $L_3$ are a substituted catecholate ligand as defined herein. When multiple substituted catecholate ligands are present, the substituted catecholate ligands can be the same or different.

In some embodiments, substituted catecholate ligands can be present in combination with unsubstituted catecholate ligands. In some embodiments, at least two of $L_1$, $L_2$ and $L_3$ can be substituted catecholate ligands and one or more of $L_1$, $L_2$ and $L_3$ can be an unsubstituted catecholate ligand. That is, in more specific embodiments, $L_1$ and $L_2$ can be a substituted catecholate ligand and $L_3$ can be an unsubstituted catecholate ligand. In some embodiments, one of $L_1$, $L_2$ and $L_3$ can be a substituted catecholate ligand and two of $L_1$, $L_2$ and $L_3$ can be an unsubstituted catecholate ligand. That is, $L_1$ can be a substituted catecholate ligand and $L_2$ and $L_3$ can be an unsubstituted catecholate ligand.

In still other various embodiments, at least one of $L_1$, $L_2$ and $L_3$ can be a substituted catecholate ligand and any of $L_1$, $L_2$ and $L_3$ that are not substituted catecholate ligands can be selected from an unsubstituted catecholate, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. In yet still other various embodiments, at least two of $L_1$, $L_2$ and $L_3$ can be a substituted catecholate ligand and any of $L_1$, $L_2$ and $L_3$ that are not a substituted catecholate ligand can be selected from an unsubstituted catecholate, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that the ligands defined in the foregoing lists can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of monodentate ligands that can optionally be present in the coordination compounds of the present disclosure include, for example, halides, cyanide, carbonyl or carbon monoxide, nitride, oxo, hydroxo, water, sulfide, thiols, pyridine, pyrazine, and the like. Other examples of bidentate ligands that can optionally be present in the coordination compounds of the present disclosure include, for example, bipyridine, bipyrazine, ethylenediamine, diols (including ethylene glycol), and the like. Other examples of tridentate ligands that can optionally be present in the coordination compounds of the present disclosure include, for example, terpyridine, diethylenetriamine, triazacyclononane, tris(hydroxymethyl)aminomethane, and the like. Other acceptable ligands can include quinones, hydroquinones, viologens, acridinium, polycyclic aromatic hydrocarbons and combinations thereof.

In general, any transition metal can be present in the coordination compounds disclosed herein. In some embodiments, the transition metal can be selected from among Al, Cr, Ti and Fe. For purposes of the present disclosure, Al is to be considered a transition metal. In more specific embodiments, the transition can be Ti. Other suitable transition and main group metals can include, for example, Ca, Co, Cu, Mg, Mn, Mo, Ni, Pd, Pt, Ru, Sn, Zn, Zr, V and any combination thereof. In various embodiments, the coordination compounds can include a transition metal in a non-zero oxidation state when the transition metal is in both its oxidized and reduced forms.

In other various embodiments, electrolyte solutions are described herein. The electrolyte solutions can include an active material that is a coordination compound containing at least one substituted catecholate ligand as defined hereinabove. That is, electrolyte solutions of the present disclosure can include the various compositions described hereinabove as an active material.

In still other various embodiments, flow batteries are described herein. The flow batteries can incorporate an electrolyte solution including an active material that is a coordination compound containing at least one substituted catecholate ligand as defined hereinabove. That is, flow batteries of the present disclosure can include an electrolyte solution containing the various compositions described hereinabove as an active material. Exemplary disclosure is presented hereinbelow regarding illustrative flow batteries and their operating characteristics when employing the presently disclosed electrolyte solutions.

In more specific embodiments, the electrolyte solutions of the present disclosure can be an aqueous solution. As used herein, the terms "aqueous solution" or "aqueous electrolyte" will refer to any solution in which water is the predominant component, including solutions containing a water-miscible organic solvent as a minority component. Illustrative water-miscible organic solvents that can be present include, for example, alcohols and glycols, optionally in the presence of one or more surfactants. In more specific embodiments, an aqueous solution can contain at least about 98% water by weight. In other more specific embodiments, an aqueous solution can contain at least about 55% water by weight, or at least about 60% water by weight, at least about 65% water by weight, at least about 70% water by weight, at least about 75% water by weight, at least about 80% water by weight, at least about 85% water by weight, at least about 90% water by weight, or at least about 95% water by weight. In some embodiments, the aqueous solution can be free of water-miscible organic solvents and consist of water alone as a solvent.

In addition to a solvent and the coordination compound active materials described above, the electrolyte solutions of the present disclosure can include one or more mobile ions. In some embodiments, mobile ions can include proton, hydronium, or hydroxide. In other various embodiments of the present disclosure, one can transport ions other than proton, hydronium, or hydroxide, either alone or in combination with proton, hydronium or hydroxide. Such additional mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other mobile ions can include, for example, ammonium and tetraalkylanmmonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide.

In further embodiments, the electrolyte solutions described herein can also include one or more additional additives such as, but not limited to, a buffer, a supporting electrolyte, a viscosity modifier, a wetting agent, or any combination thereof. Illustrative buffers can include, but are not limited to, salts of phosphates, borates, carbonates, silicates, tris(hydroxymethyl)aminomethane (tris), 4-(2-hydroxyethyl)-1-piperazineethanesulfonic acid (hepes), piperazine-N,N'-bis(ethanesulfonic acid) (pipes), or any combination thereof. Other examples of suitable buffers and the other additional additives will be familiar to one having ordinary skill in the art.

The electrolyte solutions of the present disclosure can exhibit any pH in a range of about 1 to about 14. In more specific embodiments, the electrolyte solutions of the present disclosure can contain the coordination complexes described hereinabove and have a pH ranging between about 1 and about 13, or between about 2 and about 12, or between about 4 and about 10, or between about 6 and about 8, or between about 1 and about 7, or between about 7 and about 13, or between about 8 and about 13, or between about 9 and about 14, or between about 10 and about 13, or between about 9 and about 12. Suitable pH ranges for the electrolyte solutions can be chosen based upon the stability and solubility of the coordination compounds and/or the ligands at a given pH, and such consideration can be determined by one having ordinary skill in the art.

In some embodiments, the electrolyte solutions of the present disclosure can have a concentration of the coordination compounds of at least about 0.5 M, more particularly a concentration ranging between 0.5 M and about 3 M. In more particular embodiments, an aqueous electrolyte solution of the present disclosure can have a concentration of the coordination compound in the aqueous solution that ranges between 0.5 M and about 3 M. In other various embodiments, a concentration of the coordination compounds in the electrolyte solution can be up to about 0.5 M, or up to about 1 M, or up to about 1.5 M, or up to about 2 M, or up to about 2.5 M, or up to about 3 M, particularly in an aqueous electrolyte solution. In more specific embodiments, a concentration of the coordination compounds in the electrolyte solution can range between about 0.5 M and about 3 M, or between about 1 M and about 3 M, or between about 1.5 M and about 3 M, or between 1 M and about 2.5 M. In other more specific embodiments, a concentration of the coordination compounds can range between about 1 M and about 1.8 M in an aqueous electrolyte solution.

In some embodiments, the electrolyte solutions of the present disclosure can provide high open circuit voltages within a flow battery. For example, when the electrolyte solutions contain a titanium coordination complex of the substituted catecholate ligands, the open circuit voltage can be at least about 0.8 V, or at least about 0.9 V, or at least about 1.0 V, or at least about 1.1 V, or at least about 1.2 V, or at least about 1.3 V, or at least about 1.4 V, or at least about 1.5 V, or at least about 1.6 V, or at least about 1.7 V, or at least about 1.8 V, or at least about 1.9 V, or at least about 2.0 V. These open circuit voltages can be realized in a flow battery in which the electrolyte solution is incorporated.

Illustrative flow batteries that can incorporate the foregoing coordination compounds and electrolyte solutions will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like and any combination thereof.

Further, it is to be appreciated that while the disclosure herein is generally directed to flow batteries, other electrochemical energy storage media can incorporate the electrolyte solutions described herein, specifically those utilizing stationary electrolytes.

In some embodiments, flow batteries of the present disclosure can include: a first chamber containing a negative electrode contacting a first aqueous electrolyte; a second chamber containing a positive electrode contacting a second aqueous electrolyte, and a separator disposed between the first and second electrolytes. The electrolyte chambers provide separate reservoirs within the cell, through which the first and/or second electrolytes circulate so as to contact the respective electrodes and the separator. Each chamber and its associated electrode and electrolyte define a corresponding half-cell. The separator provides several functions which include, for example, (1) serving as a barrier to mixing of the first and second electrolytes, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolytes can be transported from separate storage tanks through the corresponding electrolyte chambers. In a charging cycle, electrical power can be applied to the cell such that the active material contained in the second electrolyte undergoes a one or more electron oxidation and the active material in the first electrolyte undergoes a one or more electron reduction. Similarly, in a discharge cycle the second electrolyte is reduced and the first electrolyte is oxidized to generate electrical power.

In more specific embodiments, illustrative flow batteries of the present disclosure can include: (a) a first aqueous electrolyte containing a first coordination compound; (b) a second aqueous electrolyte containing a second coordination compound; (c) a separator positioned between said first and second aqueous electrolytes; and (d) a mobile ion in the first and second aqueous electrolytes. As described in more detail below, the separator can be an ionomer membrane, and it can have a thickness of less than 100 microns and have an associated net charge that is the same sign as that of the first and second coordination compounds. In some embodiments, at least one of the first and second coordination compounds can include a substituted catecholate ligand, as described hereinabove. In other various embodiments, one of the first and second coordination compounds can be a redox couple of ferricyanide [$Fe(CN)_6^{3-}$] and ferrocyanide [$Fe(CN)_6^{4-}$]. In more specific embodiments, the ferricyanide/ferrocyanide redox couple can be used as a first coordination compound and the second coordination compound can be a coordination compound containing a substituted catecholate ligand, particularly a titanium coordination compound containing these types of ligands.

FIG. 1 depicts a schematic of an illustrative flow battery. Unlike typical battery technologies (e.g., Li-ion, Ni-metal hydride, lead-acid, and the like), where active materials and other components are housed in a single assembly, flow batteries transport (e.g., via pumping) redox active energy storage materials from storage tanks through an electrochemical stack. This design feature decouples the electrical energy storage system power from the energy storage capacity, thereby allowing for considerable design flexibility and cost optimization.

As shown in FIG. 1, flow battery system 1 includes an electrochemical cell that features separator 20 (e.g., a membrane) that separates the two electrodes 10 and 10' of the electrochemical cell. Electrodes 10 and 10' are formed from a suitably conductive material, such as a metal, carbon, graphite, and the like. Tank 50 contains first active material 30, which is capable of being cycled between an oxidized and reduced state. For example, first active material 30 can be a coordination compound containing a substituted catecholate ligand.

Pump 60 affects transport of first active material 30 from tank 50 to the electrochemical cell. The flow battery also suitably includes second tank 50' that contains second active material 40. Second active material 40 can be the same material as active material 30, or it can be different. For example, second active material 40 can be ferricyanide/ferrocyanide, as described above. Second pump 60' can affect transport of second active material 40 to the electrochemical cell. Pumps can also be used to affect transport of the active materials from the electrochemical cell back to tanks 50 and 50' (not shown in FIG. 1). Other methods of affecting fluid transport, such as siphons, for example, can also suitably transport first and second active materials 30 and 40 into and out of the electrochemical cell. Also shown in FIG. 1 is power source or load 70, which completes the circuit of the electrochemical cell and allows a user to collect or store electricity during its operation.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow battery system can include one or more active materials that are solids, gases, and/or gases dissolved in liquids. Active materials can be stored in a tank, in a vessel open to the atmosphere, or simply vented to the atmosphere.

As used herein, the terms "separator" and "membrane" refer to an ionically conductive and electrically insulating material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to a polymer membranes containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—$CF$=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer, and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depends on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination compound, the average diameter of the coordination compound can be about 50% greater than the average pore size of the porous membrane. On the other hand, if a porous membrane has substantially uniform pore sizes, the average diameter of the coordination compound can be about 20% larger than the average pore size of the porous membrane. Likewise, the average diameter of a coordination compound is increased when it is further coordinated with at least one water molecule. The diameter of a coordination compound of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, less than about 300 micrometers, less than about 250 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, or less than about 10 micrometers. Suitable separators can include those in which the flow battery is capable of operating with a current efficiency of greater than about 85% with a current density of 100 Ma/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 Ma/cm$^{-2}$. In further embodiments, suitable separators can include those in which the flow battery is capable of operating at a voltage efficiency of greater than 70%, greater than 80% or even greater than 90%.

The diffusion rate of the first and second active materials through the separator can be less than about $1\times10$ mol cm$^{-2}$ day$^{-1}$, less than about $1\times10^6$ mol cm$^{-2}$ day$^{-1}$, less than about $1\times10^{-2}$ mol cm$^{-2}$ day$^{-1}$, less than about $1\times10^{-9}$ mol cm$^{-2}$ day$^{-1}$, less than about $1\times10^{-11}$ mol cm$^{-3}$ day$^{-1}$, less than about $1\times10^{-13}$ mol cm$^{-2}$ day$^{-1}$, or less than about $1\times10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where, the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 pin, less than about 75 μm, less than about 50 μm, or less than about 250 μm; (f) where the flow battery is capable of operating at a current density of greater than about 100 mA/cm$^2$ with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow batter (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad (1)$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad (2)$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 3

$$\text{Charge density} = (26.8 \text{ A-h/mol}) \times [\text{active material}] \times N \quad (3)$$

where [active material] and N are as defined above.

As used herein, the term "current density" will refer to the total current passed in an electrochemical cell divided by the geometric area of the electrodes of the cell and is commonly reported in units of $mA/cm^2$.

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{EFF,RT} = V_{discharge}/V_{charge} \times 100\% \quad (4)$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

Examples

The substituted catecholate ligands described above can be prepared using conveniently available starting materials using conventional coupling reactions. For example, 1,2,3 trihydroxybenzene and 1,2,4 trihydroxybenzene are commercially available and can be functionalized to prepare some of the substituted catecholate ligands described herein. Similarly, d,l-3,4-dihydroxymandelic acid, protocatechuic aldehyde, or protocatechuic acid (e.g., see FIG. 2) can be used as starting materials for preparing some of the substituted catecholate ligands described herein. In some cases, it can be useful to protect the 1,2-hydroxyls of the catechol framework, for example, by reacting with ethylene or propylene glycol, before further functionalization. Non-cyclical protecting group strategies can be used as well. Similarly, α-hydroxy catecholcarboxylic acids, catecholamines, polyols, polyolcarboxy acids, amino acids, and amines are also accessible either commercially or synthetically and can be used in preparing the substituted catecholate ligands.

With ligands in hand, titanium complexes can be prepared by a variety of methods. For example, tris-catecholate complexes, including mixed salt complexes, can be prepared by known methods. See, e.g., Davies, J. A.; Dutramez, S. *J. Am. Ceram. Soc.* 1990, 73. 2570-2572 (from titanium(IV) oxysulfate and pyrocatechol), and Raymond, K. N.; Isied, S. S., Brown, L. D.; Fronczek, F. R.; Nibert, J. H. *J. Am. Chem. Soc.* 1976, 98, 1767-1774. Biscatecholate complexes (e.g., sodium potassium titanium(IV) biscatecholate monolactate, sodium potassium titanium (IV) biscatecholate monogluconate, sodium potassium titanium(IV) biscatecholate monoascorbate, and sodium potassium titanium(IV) bis catecholate monocitrate) can be made from a titanium catecholate dimer, $Na_2K_2[TiO(catecholate)]_2$. See Borgias, B. A.; Cooper, S. R.; Koh, Y. B.; Raymond, K. N. *Inorg. Chem.* 1984, 23, 1009-1016. Such syntheses have also been described in U.S. Pat. Nos. 8,753,761 and 8,691,413, which are incorporated by reference herein, at least for their synthetic descriptions and electrochemical data.

Table 1 below shows electrochemical data for various titanium bis- and tris-catecholate coordination compounds.

TABLE 1

| Couple | $E_{1/2}$, V vs. RHE | pH |
|---|---|---|
| Ti(catecholate)$_3^{2-/3-}$ | −0.45 | 11 |
| Ti(pyrogallate)$_3^{2-/3-}$ | −0.55 | 9.8 |
| Ti(catecholate)$_2$(pyrogallate)$^{2-/3-}$ | −0.50 | 11 |
| Ti(catecholate)$_2$(ascorbate)$^{2-/3-}$ | −0.55 | 10 |
| Ti(catecholate)$_2$(gluconate)$^{2-/3-}$ | −0.60 | 9 |
| Ti(catecholate)$_2$(lactate)$^{2-/3-}$ | −0.49 | 9 |
| Ti(catecholate)(pyrogallate)(lactate)$^{2-/3-}$ | −0.70 | 8.5 |
| Ti(citrate)$_3$ | −0.04 | 5 |

Although the disclosure has been described with reference to the disclosed embodiments, those skilled in the art will readily appreciate that these only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:
1. A composition comprising:
   a coordination compound comprising a substituted catecholate ligand, the substituted catecholate ligand having a structure of

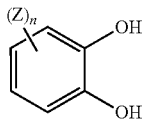

in a neutral form or a salt form;
   wherein n is an integer ranging between 1 and 4, such that one or more Z are bound to the substituted catecholate ligand at an open aromatic ring position, each Z being the same or different when more than one Z is present; and
   wherein Z is a heteroatom functional group selected from the group consisting of $A^1R^{41}$, $A^2R^{42}$, $A^3R^{43}$, and CHO;
   wherein $A^1$ is —$(CH_2)_a$— or —$(CHOR)(CH_2)_a$—, $R^{41}$ is —$OR^1$ or —$(OCH_2CH_2O)_bR^1$, a is an integer ranging between 0 and about 6, with the proviso that $R^1$ is not H when a is 0 and $R^{41}$ is —$OR^1$, and b is an integer ranging between 1 and about 10;
   wherein R is H, $C_1$-$C_6$ alkyl, heteroatom-substituted $C_1$-$C_6$ alkyl, or $C_1$-$C_6$ carboxyalkyl; and
   wherein $R^1$ is H, methyl, ethyl, a $C_2$-$C_6$ polyol bound through an ether linkage or an ester linkage, or $C_1$-$C_6$ carboxyalkyl;
   wherein $A^2$ is —$(CH_2)_c$— or —$CH(OR^2)(CH_2)_d$—, $R^{42}$ is —$NR^3R^4$, a carbon-linked amino acid, or —C(=O)$XR^5$, X is —O— or —$NR^6$—, c is an integer ranging between 0 and about 6, and d is an integer ranging between 0 and about 4;
   wherein $R^2$, $R^3$, $R^4$ and $R^6$ are independently selected from the group consisting of H, $C_1$-$C_6$ alkyl, or heteroatom-substituted $C_1$-$C_6$ alkyl; and
   wherein $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or —$(CH_2CH_2O)_bR^1$; and
   wherein $A^3$ is —O— or —$NR^2$—, $R^{43}$ is —$(CHR^7)_eOR^1$, —$(CHR^7)_eNR^3R^4$, —$(CHR^7)_eC(=O)XR^5$, or —C(=O)$(CHR^7)_fR^8$, e is an integer ranging between 1 and about 6, with the proviso that e is not 1 when $A^3$ is —O—, and f is an integer ranging between 0 and about 6;
   wherein $R^7$ is H or OH;
   wherein $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —$(OCH_2CH_2O)_bR^1$;
   wherein the substituted catecholate ligand has a structure selected from the group consisting of

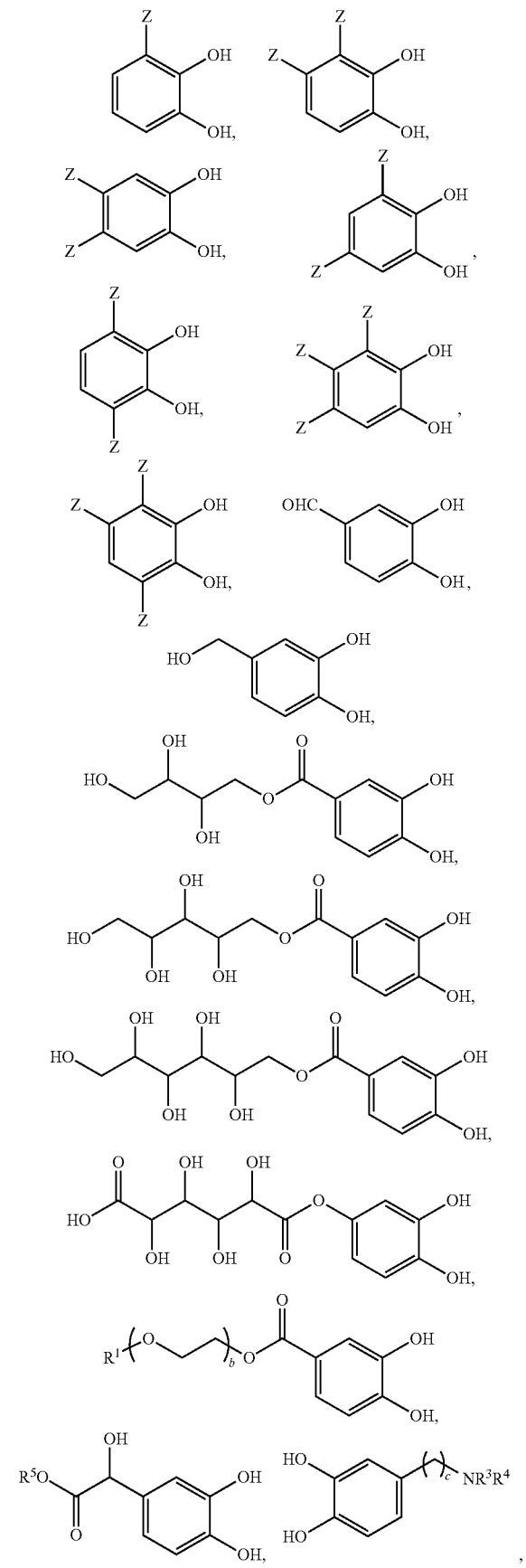

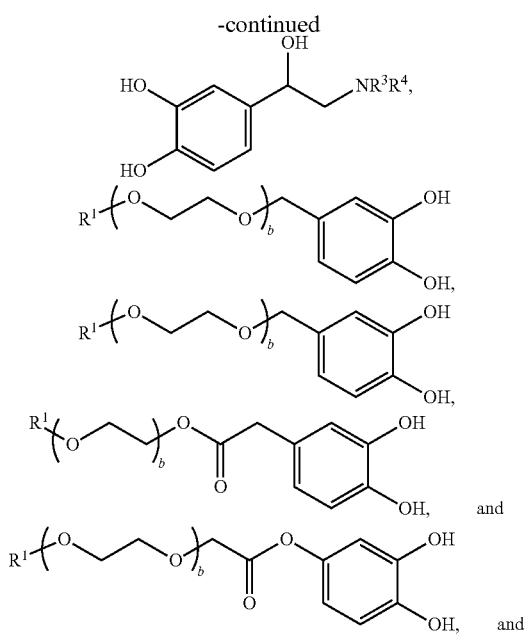

wherein the coordination compound has a formula of
$D_gM(L_1)(L_2)(L_3)$;

wherein M is a transition metal, D is $NH_4^+$, $Li^+$, $Na^+$, or $K^+$, g is an integer ranging between 0 and 6, and $L_1$, $L_2$ and $L_3$ are ligands, at least one of $L_1$, $L_2$ and $L_3$ being the substituted catecholate ligand.

2. The composition of claim 1, wherein at least two of $L_1$, $L_2$ and $L_3$ are substituted catecholate ligands.

3. The composition of claim 2, wherein $L_1$ and $L_2$ are substituted catecholate ligands and $L_3$ is an unsubstituted catecholate ligand.

4. The composition of claim 1, wherein $L_1$ is the substituted catecholate ligand and $L_2$ and $L_3$ are unsubstituted catecholate ligands.

5. The composition of claim 1, wherein each of $L_1$, $L_2$ and $L_3$ are substituted catecholate ligands.

6. The composition of claim 1, wherein the transition metal is Ti.

7. The composition of claim 1, wherein any of $L_1$ to $L_3$ that are not the unsubstituted catecholate ligand comprises one or more ligands that are independently selected from the group consisting of an unsubstituted catecholate, ascorbate, citrate, glycolate, a polyol, gluconate, a hydroxyalkanoate, acetate, formate, benzoate, malate, maleate, phthalate, sarcosinate, salicylate, oxalate, a urea, a polyamine, aminophenolate, acetylacetonate, and lactate.

8. An electrolyte solution comprising the composition of claim 1.

9. The electrolyte solution of claim 8, wherein the electrolyte solution is an aqueous solution.

10. The electrolyte solution of claim 9, further comprising:
a buffer, a supporting electrolyte, a viscosity modifier, a wetting agent, or any combination thereof.

11. The electrolyte solution of claim 9, wherein the aqueous solution has a pH ranging between about 1 and about 13.

12. The electrolyte solution of claim 9, wherein the transition metal is Ti.

13. The electrolyte solution of claim 9, wherein a concentration of the coordination compound in the aqueous solution ranges between about 0.5 M and about 3 M.

14. A flow battery comprising an electrolyte solution comprising the composition of claim 1.

15. The flow battery of claim 14, wherein the transition metal is Ti.

* * * * *